United States Patent
Howarth et al.

(10) Patent No.: US 6,749,758 B2
(45) Date of Patent: Jun. 15, 2004

(54) METHODS AND SYSTEMS FOR UNIFORM-CONTROL OF BROMINE CONCENTRATIONS IN WATER

(75) Inventors: Jonathan N. Howarth, Baton Rouge, LA (US); Michael J. Sanders, Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 173 days.

(21) Appl. No.: 10/010,296

(22) Filed: Dec. 5, 2001

(65) Prior Publication Data

US 2003/0102271 A1 Jun. 5, 2003

(51) Int. Cl.⁷ .................................................. C02F 1/76
(52) U.S. Cl. ...................... 210/746; 210/752; 210/755; 210/764; 422/3; 422/37
(58) Field of Search ................................ 210/754, 755, 210/752, 746, 764; 422/37, 3

(56) References Cited

U.S. PATENT DOCUMENTS

| | | | |
|---|---|---|---|
| 3,412,021 A | 11/1968 | Paterson | 210/62 |
| 4,532,330 A | 7/1985 | Cole | 548/311 |
| 4,550,011 A | 10/1985 | McCollum | 422/68 |
| 4,621,096 A | 11/1986 | Cole | 514/389 |
| 4,677,130 A | 6/1987 | Puzig | 514/389 |
| 4,698,165 A | 10/1987 | Theyson | 210/755 |
| 4,752,740 A | 6/1988 | Steininger | 324/438 |
| 4,767,511 A | 8/1988 | Aragon | 204/128 |
| 5,264,136 A | 11/1993 | Howarth et al. | 210/754 |
| 5,268,092 A | 12/1993 | Eden | 210/96.1 |
| 5,422,014 A | 6/1995 | Allen et al. | 210/743 |
| 5,422,126 A | 6/1995 | Howarth et al. | 424/723 |
| 5,565,109 A * | 10/1996 | Sweeny | 210/755 |
| 5,641,520 A | 6/1997 | Howarth et al. | 424/723 |
| 5,662,940 A | 9/1997 | Hight et al. | 424/661 |
| 5,750,061 A | 5/1998 | Farina et al. | |
| 5,780,641 A | 7/1998 | Yerushalmi et al. | 548/320.5 |
| 5,888,428 A | 3/1999 | Howarth et al. | 252/403 |
| 6,007,726 A * | 12/1999 | Yang et al. | 210/752 |
| 6,086,746 A | 7/2000 | Nalepa | 205/500 |
| 6,125,481 A | 10/2000 | Sicilano | 4/509 |
| 6,143,184 A | 11/2000 | Martin et al. | 210/743 |
| 6,149,819 A | 11/2000 | Martin et al. | 210/743 |
| 6,171,480 B1 | 1/2001 | Lee et al. | 210/85 |
| 6,303,038 B1 * | 10/2001 | Sanders et al. | 210/754 |
| 6,478,972 B1 * | 11/2002 | Shim et al. | 210/755 |

FOREIGN PATENT DOCUMENTS

| | | |
|---|---|---|
| EP | 0 427 517 A1 | 5/1991 |
| GB | 1358617 | 7/1974 |
| WO | 9304987 | 3/1993 |
| WO | 9743215 | 11/1997 |
| WO | 0034186 | 6/2000 |

OTHER PUBLICATIONS

McCollum, Roy, "Should You Automate Your Pool and Spa?", Club Business, 1987, Oct., 2 pages.

* cited by examiner

*Primary Examiner*—Peter A. Hruskoci
(74) *Attorney, Agent, or Firm*—Edgar E. Spielman, Jr.

(57) ABSTRACT

Reduced stabilization time of oxidation-reduction potential is achieved in a recreational body of water by baseloading bromide ions and dialkylhydantoin prior to biocidal treatment of the water body with N,N'-dihalo-5,5-dialkylhydantoin.

35 Claims, No Drawings

METHODS AND SYSTEMS FOR UNIFORM-CONTROL OF BROMINE CONCENTRATIONS IN WATER

TECHNICAL FIELD

This invention relates to, and has among its objectives, biocidal treatment of water bodies so that stable response of an oxidation-reduction potential sensor is provided.

REFERENCE TO COMMONLY-OWNED APPLICATIONS

Commonly-owned application Ser. No. 09/323,348, filed Jun. 1, 1999, now U.S. Pat. No. 6,303,038 B1, issued Oct. 16, 2001, describes solid mixtures of dialkylhydantoins and bromide ion sources for water sanitation. Commonly-owned copending application Ser. No. 09/484,844, filed Jan. 18, 2000, describes chemical processes from which compositions of the present invention can be formed or derived. Commonly-owned application Ser. No. 09/484,687, filed Jan. 18, 2000, now U.S. Pat. No. 6,508,954 B1, issued Jan. 21, 2003, describes 1,3-dibromo-5,5-dimethylhydantoin particulate solids producible by the processes of Application Ser. No. 09/484,844, such solids having unprecedented enhanced properties, and compacted articles made from such particulate solids without use of a binder. Commonly-owned application Ser. No. 09/483,896, filed Jan. 18, 2000, now U.S. Pat. No. 6,448,410 B1, issued Sep. 10, 2002, relates to the granulation of small average particle size 1,3-dibromo-5,5-dimethylhydantoin and also to the compaction of such granulated products to form larger-sized articles. Commonly-owned application Ser. No. 09/484,891, filed Jan. 18, 2000, now U.S. Pat. No. 6,495,698 B1, issued Jan. 17, 2003, relates to the compacting of 1,3-dihalo-5,5-dimethylhydantoins other than 1,3-dibromo-5,5-dimethylhydantoin without use of binders, and to the novel compacted forms so produced. Commonly-owned application Ser. No. 09/484,938, filed Jan. 18, 2000, now U.S. Pat. No. 6,565,868 B1, issued May 20, 2003, describes using 1,3-dibromo-5,5-dimethylhydantoin for microbiological or biofilm control in water. Commonly-owned copending application Ser. No. 09/487,816, filed Jan. 18, 2000, relates in part to converting 1,3-dihalo-5,5-dimethylhydantoins into compacted articles using novel binders. Commonly-owned copending application Ser. No. 09/775,516, filed Feb. 2, 2001, describes microbiological control in aqueous media achieved by introducing a microbiocidally effective quantity of one or more 1,3-dibromo-5,5-dialkylhydantoins into the aqueous medium. Commonly-owned copending application Ser. No. 09/778,228, filed Feb. 2, 2001, describes biocidally-active 1,3-dibromo-5,5-dialkylhydantoin biocidal compositions in readily identifiable forms. Commonly-owned copending application Ser. No. 09/893,581, filed Jun. 28, 2001, describes microbiological control in poultry processing using a halogen-based microbiocide or 1,3-dihalo-5,5-alkylhydantoin.

BACKGROUND

It is the goal of any owner or operator of recreational water bodies, swimming pools, spas, hot tubs or the like to provide pool water which is maintained so that there are no detrimental microorganisms. To this end, the pool owner or operator may choose from a wide variety of biocidal chemical systems to ensure that a biocidally effective amount of water-treating agents is present in the water body on a continuous basis.

The more commonly used biocidal agents are halogen-containing biocides. As referred to herein, halogen or halo- refers to either chlorine or bromine. These agents register as "free chlorine" or "available chlorine" species in commonly used testing procedures. Persons using biocidal agents in the biocidal treatment of water customarily, if not universally, refer to "free chlorine" level as a measure of biocidal control, even though the agent may contain bromine as the oxidizing species. The EPA has determined that a level of 1.0–1.5 ppm of available chlorine should be maintained at all times to continuously kill the microorganisms and algae in such water systems. The active bromine level may be expressed as free chlorine for ease of comparison to industry standards. For example, the biocide, 1,3-dibromo-5,5-dimethylhydantoin, hydrolyzes into 2 molecules of HOBr, which registers as "free chlorine" species in commonly-used standard test procedures for determining the quantity of halogen-containing microbiocidal agent to be used for water treatment. To convert such chlorine values to active bromine values, the chlorine value should be multiplied by 2.25. Thus, in bromine-containing systems sanitation is maintained when the active bromine, as $Br_2$, is 2.0 to 3.0 ppmw.

Among the available techniques for indicating the concentration of biocidal agent present in the water system, two are used most often. In the more preferred system, an electronic Oxidation-Reduction Potential (ORP) sensor, linked to a controller device, is a sophisticated and labor efficient tool for indicating a level of halogen present which is consistent with satisfactory sanitation quality. Therefore, many commercial pool operators and some private pool owners possess ORP (Oxidation-Reduction Potential) monitoring probes interfaced to a controller. The controller electronically actuates a valve to control a flow of water to a chemical feeding device or activates a delivery pump for delivery of a biocidal chemical to the water system. When a sensing electrode of either platinum or gold, comes in contact with a solution containing species for which the probe is sensitive, an electrical potential develops at the electrode's surface. The magnitude of the potential relates to the concentration of the species being measured, so that the higher the potential, the higher the species concentration. In a recreational pool situation, the species present which presents a variation in concentration causing a change in potential is the active species of the biocidal chemical, such as active bromine. The ORP reading may be equated to the concentration of the active bromine and reported as a "free chlorine" value as per the industry naming convention. The ORP probe is pre-set to a particular mV range and will signal the controller when the mV condition deviates outside this range necessitating addition of the appropriate biocidal chemical. When sufficient amount of biocidal chemical has been delivered to the water such that the pre-set ORP condition is attained, the controller de-activates the switch to the feeding device so that no more biocidal chemical is released into the water.

The use of an ORP sensor allows the pool operator to measure the potential generated by the active form of the biocidal chemical. Additionally, ORP monitoring has an advantage in that it is an ongoing electronic process requiring no test chemicals or agents after initial stabilization. Monitoring of sanitation levels is constantly performed as opposed to being performed on some predetermined schedule basis.

Another method of water management and treatment is use of the DPD test kit which utilizes a chemical reaction between a water sample, N,N'-diethyldiphenylenediamine (DPD) and a buffer to cause a color change which can be visibly compared to a color chart of halogen concentrations. The use of a DPD test kit by a pool operator or pool technician requires the operator to sample the water, add appropriate reagent(s) and visually compare the color change of the pool water sample against a color standard chart to arrive at an approximation of the active chlorine or bromine value. If the operator employs the DPD test as the sole monitoring method, the operator, after testing, must take steps to add an appropriate biocidally effective amount of the treatment agent to the water. Thus this method tends to require more time and effort than the ORP method.

Typically, the operator will employ the DPD test kit procedure as a check on the ORP sensor reading during the initial stabilization time interval of the ORP sensor reading in a water facility which has been drained and re-filled or in which the biocidal agent is being changed.

When the pool ORP monitoring system is initially started up, either with untreated water or with water in which the biocidal agent of choice is to be changed, e.g. from a chlorine-containing system to a bromine-containing system, the pool operator may observe a phenomenon known as "ORP bounce" for as long as several weeks. ORP bounce describes a condition where, for the same active bromine residual quantity in the water, different (usually lowered) ORP responses are detected. This situation seems to be transient, and the water system eventually becomes stabilized. Having a system which exhibits a long stabilization time for the ORP reading creates a labor intensive situation for the pool operator. The operator must frequently check the ORP reading against a manually determined DPD test kit halogen value to ensure correct treatment by the automatic controller system.

When a body of water has been initially treated with N,N'-dihalo-5,5-dialkylhydantoin, it has been observed that, though the independent DPD test yields a steady value of bromine, the ORP mV reading is inconsistent. Because the ORP sensed value is vital to the proper functioning of the controller, the operator must frequently re-adjust the ORP reading when it falls to prevent a false ORP reading from triggering the addition of too much biocidal agent by the controller.

It would be advantageous if a method could be found that would significantly shorten the stabilization time period of a newly started up recreational body of water so that ORP values would quickly and reliably indicate satisfactory active bromine levels.

BRIEF SUMMARY OF THE INVENTION

This invention provides an efficient and effective way of reducing the stabilization time of a newly started up recreational body of water.

This invention involves, inter alia, the discovery that, where biocidal treatment with N,N-dihalo-5,5-dialkylhydantoin is being initialized in a recreational water body, baseloading the water with some bromide ion and dialkylhydantoin stabilizes the ORP response in a matter of hours rather than over several weeks. Thus, a method of overcoming the highly undesirable and lengthy "ORP bounce" condition has been found where, heretofore, no solution for this problem existed.

An embodiment of the invention is a process for stabilizing the oxidation-reduction potential of a recreational body of water before initially treating the water with one or more N,N-dihalo-5,5-dialkylhydantoins. The process comprises baseloading the water with bromide ion and dialkylhydantoin and thereafter treating the water with at least one N,N-dihalo-5,5-dialkylhydantoin. Use of this process can substantially shorten the time required for the ORP sensor reading to stabilize.

Another embodiment of this invention is a method of reducing the interval of time of stabilizing the oxidation-reduction potential of a recreational body of water which has not been treated with an N,N'-dihalo-5,5-dialkylhydantoin biocidal agent or which does not contain residues resulting from prior addition thereto of an N,N'-dihalo-5,5-dialkylhydantoin biocidal agent, which method comprises conducting the following steps:

A) introducing into said body of water at least one water-soluble source of bromide ion and at least one dialkylhydantoin, in which the alkyl groups each contain independently in the range of 1 to about 4 carbon atoms; then B) introducing into said body of water at least one N,N'-dihalo-5,5-dialkylhydantoin in which one halogen atom is a bromine atom and the other halogen atom is either a bromine atom or a chlorine atom, and in which one alkyl group is a methyl group and the other alkyl group contains in the range of 1 to about 4 carbon atoms; and C) determining when the oxidation-reduction potential of said body of water has become stabilized.

Use of the methods of this invention results in substantial reduction in the period of time required for the treated body of water such as a swimming pool, spa, or the like, to achieve a stable oxidation-reduction potential. Concurrently the methods of this invention shorten the period of time required for the treated water to reach the point at which one can be assured that the active bromine content of the treated water is at a suitable biocidal concentration, as determined by means of an ORP controller equipped with an ORP sensor probe. Consequently, rather than having to wait for a period of, say, three weeks before such ORP stability has been achieved, persons can make use of the stabilized, treated body of water much sooner. Moreover, the pool operator has the assurance that the body of water being used contains the requisite biocidal concentration of active bromine as indicated by the ORP controller readings.

A further embodiment of this invention is a recreational body of water is described to which has been added in sequence, bromide ion, dialkylhydantoin, and N,N-dihalo-5,5-dialkylhydantoin. The body of water, after the additions, has a stable ORP sensor reading.

The alkyl groups of the dialkylhydantoin each contain independently in the range of 1 to about 4 carbon atoms. In the N,N-dihalo-5,5-dialkylhydantoin, one halogen atom is a bromine atom and the other halogen atom is a bromine atom or a chlorine atom, and one alkyl group is a methyl group and the other alkyl group contains in the range of 1 to about 4 carbon atoms.

Other embodiments, features, and advantages of this invention will be still further apparent from the ensuing description and appended claims.

DETAILED DESCRIPTION OF THE INVENTION

Typically, when a water system is being started up with ORP sensor capability, the operator will use the manual DPD test procedure as an independent verification of the correlation between the ORP reading and the active bromine concentration of the water until stable ORP readings develop. In this context, stable ORP reading, substantially stable mV reading, substantially constant ORP and substantially stable ORP are taken to mean that the ORP mV reading or response has no greater than 5 mV plus or minus the pre-set ORP mV value when compared to independently determined active bromine values that do not themselves vary.

Additionally, this stabilization process may be viewed as an optimization of the stabilization time, such that the length of time of ORP bounce is substantially shortened by the practice of the methods of this invention.

The period of time required to attain such a stable ORP reading may be as great as 3 weeks. In the practice of this invention, this long stabilization period may be shortened to about 1 to 10 hours, and more desirably from about 1–6 hours.

Typically the sources of bromide ion are water-soluble inorganic bromide salts. Sources of bromide ion may thus include alkali or alkaline earth metal bromide salts which are water-soluble. Naturally, for treating water to which persons or animals will or may be exposed (swimming pools, spas, etc.) the toxicological properties of the bromide salt should be taken into consideration. Among those salts of most interest are the bromide salts of sodium, calcium, magnesium, potassium, or lithium. Aqueous HBr acid and quaternary ammonium bromide are also useful in proper concentrations. Of these bromide ion sources, sodium bromide is more preferred as a safe, relatively inexpensive and readily available source of bromide ions.

For typical water treatment systems bromide ion concentrations should be in the range of about 5 ppmw to about 50 ppmw, and preferably in the range of about 10 to about 20 ppmw. Departures from the foregoing ranges are permissible whenever deemed necessary or desirable without departing from the scope of this invention.

The water-soluble dialkylhydantoins utilized in the practice of this invention are those in which the alkyl groups are alkyl groups each having in the range of 1 to 4 carbon atoms. Thus the dialkylhydantoins used in this invention comprise 5,5-dimethylhydantoin, 5,5-diethylhydantoin, 5,5-di-n-propylhydantoin, 5,5-diisopropylhydantoin, 5,5-di-n-butylhydantoin, 5,5-diisobutylhydantoin, 5,5-di-sec-butylhydantoin, 5,5-di-tert-butylhydantoin, 5-ethyl-5-methylhydantoin, 5-n-propyl-5-methylhydantoin, 5-isopropyl-5-methylhydantoin, 5-n-butyl-5-methylhydantoin, 5-isobutyl-5-methylhydantoin, 5-sec-butyl-5-methylhydantoin, 5-tert-butyl-5-methylhydantoin, 5-ethyl-5-n-propylhydantoin, 5-ethyl-5-isopropylhydantoin, 5-ethyl-5-n-butylhydantoin, 5-ethyl-5-isobutylhydantoin, 5-ethyl-5-sec-butylhydantoin, 5-ethyl-5-tert-butylhydantoin, 5-isopropyl-5-n-propylhydantoin, 5-n-butyl-5-n-propylhydantoin, 5-n-propyl-5-sec-butylhydantoin, 5-n-propyl-5-isobutylhydantoin, 5-n-propyl-5-tert-butylhydantoin, 5-isopropyl-5-n-butylhydantoin, 5-isopropyl-5-sec-butylhydantoin, 5-isobutyl-5-isopropylhydantoin, 5-isopropyl-5-tert-butylhydantoin, 5-isobutyl-5-n-butylhydantoin, 5-n-butyl-5-sec-butylhydantoin, 5-n-butyl-5-tert-butylhydantoin, 5-isobutyl-5-sec-butylhydantoin, 5-isobutyl-5-tert-butylhydantoin and 5-sec-butyl-5-tert-butylhydantoin. The most preferred dialkylhydantoin employed in the practice of this invention is 5,5-dimethylhydantoin.

The amounts in which the water-soluble dialkylhydantoins are used can vary within reasonably wide limits. Generally speaking, amounts in the range of about 5 to about 50 ppmw are suitable. Preferably the amounts used are in the range of about 10 to about 20 ppmw. In the case of 5,5-dimethylhydantoin, a particularly preferred amount is in the range of about 15 ppmw to about 20 ppmw. Departures from the foregoing ranges are permissible whenever deemed necessary or desirable without departing from the scope of this invention.

The source of bromide ion and 5,5-dialkylhydantoin may be introduced into the body of water either separately or in combination. The combination of the bromide ion and 5,5-dialkylhydantoin preferably is in the form of a pre-mixed, pre-packaged composition as use of such pre-mixed, pre-packaged compositions ensures delivery of a more accurate quantity of these components, minimizes the likelihood of blending errors and in general simplifies the mode of addition. Preferably, such pre-mixed, pre-packaged compositions are in the form of a dry powder or granules. However, it is also convenient pursuant to this invention to provide such pre-mixed, pre-packaged compositions in the form of aqueous concentrates. Whether these components are introduced into the body of water separately or in combination (e.g., preferably as a pre-mixed or pre-packaged composition), the components are typically employed in a ratio of about 1 to about 10 parts by weight of dialkylhydantoin per each part by weight of the source of bromide ion. Preferably, this ratio is in the range of about 2 to about 5 parts by weight of dialkylhydantoin per each part by weight of the source of bromide ion. A particularly preferred pre-mixed, pre-packaged composition of this invention is composed of sodium bromide and dimethylhydantoin as a 30:70 wt % mixture, respectively. The package of these components in this ratio is preferably in the form of 2 pound packages which enables the water to be dosed, for example, at a preferred pool dosage rate of about 2 pounds per 10,000 gallons of pool capacity. The preferred dosage rate for pools of greater or lesser capacity can be readily calculated by the pool operator on the basis of the known capacity of the pool. The 2-pound packages of the sodium bromide/dimethylhydantoin mixture may thus aid in easily baseloading pools of various capacities when utilized in the practice of this invention. Of course, packages with other total dosage levels of these pre-mixed components in the package (e.g., 1-pound, 5-pounds, 10-pounds, etc.) are within the scope of this invention.

The water-soluble N,N'-dihalo-5,5-dialkylhydantoins utilized in the practice of this invention are those in which one of the alkyl groups in the 5-position is a methyl group and the other alkyl group in the 5-position is an alkyl group having in the range of 1 to 4 carbon atoms. Thus use can be made of such compounds as 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, N,N'-bromochloro-5,5-dimethylhydantoin, N,N'-bromochloro-5-ethyl-5-methylhydantoin, N,N'-bromochloro-5-n-propyl-5-methylhydantoin, N,N'-bromochloro-5-isopropyl-5-methylhydantoin, N,N'-bromochloro-5-n-butyl-5-methylhydantoin, N,N'-bromochloro-5-isobutyl-5-methylhydantoin, N,N'-bromochloro-5-sec-butyl-5-methylhydantoin, N,N'-bromochloro-5-tert-butyl-5-methylhydantoin and mixtures of any two or more of them.

The preferred types of N,N'-dihalo-5,5-dialkylhydantoins are N,N'-bromochloro-5,5-dialkylhydantoins and 1,3-dibromo-5,5-dialkylhydantoins with the latter types being more preferred. Also useful are mixtures of one or more N,N'-bromochloro-5,5-dialkylhydantoins and one or more 1,3-dichloro-5,5-dialkylhydantoins. Of the N,N'-bromochloro-5,5-dialkylhydantoins, N,N'-bromochloro-5,5-dimethylhydantoin is preferred. Another N,N'-bromochloro-5,5-dialkylhydantoin composition is comprised of a mixture of N,N'-bromochloro-5,5-dimethylhydantoin, 1,3-dichloro-5-ethyl-5-methylhydantoin, and 1,3-dichloro-5,5-dimethylhydantoin wherein more than 50% by weight of the mixture is N,N'-bromochloro-5,5-dimethylhydantoin, such as, for example, a mixture in which these three components are in proportions of about 60:10.6:27.4 wt. %, respectively.

Of the 1,3-dibromo-5,5-dialkylhydantoins, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred biocide employed in the practice of this invention is 1,3-dibromo-5,5-dimethylhydantoin.

The amounts of the N,N'-dihalo-5,5-dialkylhydantoins, whether used singly or in the form of mixtures of two or more such compounds, are typically in the range of about 0.5 to about 10 ppmw of active bromine, and preferably in the range of about 1 to about 4 ppmw of active bromine. The active bromine concentration, when employing 1,3-dibromo-5,5-dimethylhydantoin and/or N,N'-bromochloro-5,5-dimethylhydantoin, is preferably in the range of about 1 ppmw to about 10 ppmw as active $Br_2$. Departures from the foregoing ranges are permissible whenever deemed necessary or desirable without departing from the scope of this invention.

In this connection, a facet of this invention is to enable active halogen concentrations to be readily and accurately determined by measuring the oxidation-reduction potential by means of an ORP controller equipped with a sensor probe. This in turn requires that the oxidation-reduction potential of the water be in a stable condition. Thus the typical sequence of steps used in achieving the requisite concentration of active halogen in the water is as follows:

1) Baseload the body of water with the source of bromide ion and dialkylhydantoin;
2) Introduce an amount of the N,N'-dihalo-5,5-dialkylhydantoin calculated to provide a desired concentration of active halogen;
3) After a period of time during which the additives have been thoroughly mixed and dispersed throughout the water, such as after completion of one mixing cycle of the water in the system, readings of ORP are taken and the ORP readout value of the controller is reset to a standard pre-selected value for the system, typically in the range of about 700±5 mV. Concurrently, the active halogen concentration of the water is determined on samples of the water using a standard DPD test kit;
4) When the active halogen value as determined by a DPD determination corresponds to the active halogen value as determined by a reading of the ORP controller, the body of water has reached a stable ORP condition and the concentration of active halogen has been verified. In addition, thereafter, readings of the ORP controller can be used for ascertaining active halogen concentration without need for further testing by means of the DPD test procedure.

The method of the invention is practiced on a recreational body of water which requires biocidal treatment. The body of water such as a swimming pool, usually and preferably has an ORP sensor that is in contact with, or can be brought in contact with, the water.

Although in a preferred embodiment of the invention, the method of stabilizing the ORP utilizes sodium bromide as the source of bromide ion, dimethylhydantoin (DMH) as the source of dialkylhydantoin, and 1,3-dibromo-5,5-dimethylhydantoin (DBDMH) as the source of N,N'-dihalo-5,5-dialkylhydantoin, other choices for these compositions may be made as previously indicated.

Various dosage techniques for introduction of a source of bromide ion and dialkylhydantoin can be employed in the practice of this invention. Such techniques for introducing a source of bromide ion and dialkylhydantoin can include introduction of the chemicals separately or as a mixture, such as a dry mixture or an aqueous solution. Introduction of a source of bromide ion and dialkylhydantoin can be effected by manually broadcasting, placing the chemicals in the water body's skimmer basket, floating dispenser, in-line or off-line dispenser or any other means or combination of means which ensures complete dispersal of the chemicals. The N,N'-dihalo-5,5-dialkylhydantoin is typically provided in dry powder, granulated, bar, block or puck forms. Introduction of the N,N'-dihalo-5,5-dialkylhydantoin can be effected by broadcasting, placing in a floating dispenser, an in-line or off-line dispenser, an erosion feeder, or by manual or automatic activation of the ORP controller dispenser. Thus, as used herein, introducing can be defined as bringing into contact the components with the water of the recreational water body by any means or combination of means.

The body of water is either being initially started up with clean municipal water or is undergoing a change in chemical biocidal system so that a N,N'-dihalo-5,5-dialkylhydantoin is to be introduced as biocidal agent.

The most preferred bromine-based biocide, namely 1,3-dibromo-5,5-dimethylhydantoin, in the form of easy-to-use granules is available in the marketplace from Albemarle Corporation under the trade designation XtraBrom™ 111 biocide.

DPD test kits are available from numerous sources such as Leslie's Swimming Pool Supplies (Chatsworth, Calif.), Taylor Technologies, Inc. (Sparks, Md.), Hach Company (Loveland, Colo.), LaMotte Company (Chestertown, Md.), Palintest USA (Erlanger, Ky.), etc.

The ORP sensor of the ORP controller used in connection with standard operation of the water system should be capable of registering between 250 and 900 mV. The ideal range of the ORP reading is 650 to 850 mV and an even more preferred value is 700 mV. As a practical matter, any ORP reading above 700 mV is desirable. ORP sensors and control units are available from several sources such as Chemical Automation Technologies, Inc. (Gaithersburg, Md.) which provides programmable water chemistry controllers under the model names of CAT 2000 and CAT 2000 PLUS. Aquasol Controllers, Inc. (Houston, Tex.) also provides such controllers under the model names of SPC, SPC-M, WTC, WTC-P, and IND-ORP. See also U.S. Pat. No. 4,550,011 which describes equipment of this type.

A further benefit of the invention is that it artificially spikes the DMH level. DMH complexes the bromine so that it resists reversion to dissolved elemental bromine at low pH or high oxidant levels (such as after a process know as "shocking" the pool). Reversion of bromine to its elemental form causes the water to acquire an unpleasant color.

Depending upon the light conditions and the individual who makes the observation, this color ranges from a yellow to a green. It can be disconcerting to the pool owner, especially if the pool is a commercial pool open to the public, for the water to change color in this fashion.

An illustrative embodiment of the invention is a method of stabilizing the oxidation-reduction potential (ORP) of a recreational body of water, such as a swimming pool, before the pool water is initially treated with 1,3-dibromo-5,5-dimethylhydantoin (DBDMH) as a biocidal chemical. The method comprises (A) introducing into the pool water sodium bromide and dimethylhydantoin (DMH), either separately or as a mixture. This step can take place after the pool is initially filled with clean municipal water, when the biocidal system is being changed to bromine-based chemical, or while the filling operation is underway. When the sodium bromide and DMH are introduced as a mixture, sodium bromide is about 30 wt % of the mixture and DMH is about 70 wt % of the mixture. Two pounds of the mixture for each 10,000 gallons of pool water capacity is added to effect preferred ranges. A range of about 5 ppmw to 50 ppmw of bromide ion in the pool water is preferred. A range of about 15 ppmw to about 20 ppmw of DMH is preferred. Mode of introduction of the sodium bromide and DMH, either separately or as a mixture, can be effected by broadcasting, placing the sodium bromide and DMH in the pool's skimmer basket, in-line or off-line dispenser or any other means which ensures complete dispersal of the chemicals. The method also comprises (B) introducing a feed of DBDMH so that an active bromine concentration in the pool water is in the range of about 1 ppmw to about 10 ppmw as $Br_2$. The DBDMH is typically provided in dry powder, granulated, bar, block or puck forms. Introduction of the DBDMH can be effected by in-line or off-line dispenser, erosion feeder, or by manual or automatic activation of the ORP controller dispenser. The method of verification of the active bromine concentration as $Br_2$ is by use of the ORP sensor reading in which a certain mV value correlates to a ppmw of $Br_2$. An independent check of the $Br_2$ concentration is by way of a DPD test conducted according to the test kit instructions which reports active bromine concentration as $Br_2$. The pool typically has a circulation pump system which allows the electronic controller to cause introduction of the DBDMH to a pump-around loop. The swimming pool's circulation pump system provides dispersal of the sodium bromide, DMH and DBDMH once they are all introduced into the pool water. Dispersal time for complete mixing of the introduced chemicals commonly takes in the range of 2 to 6 hours, depending on the size and configuration of the pool. The ORP sensor reading from an ORP sensor probe of an ORP controller which is in contact with the pool water is typically pre-set before (A) to 700 mV. Allowing for adequate dispersal time after (B), the ORP sensor reading is monitored at regular intervals. A manual DPD test is conducted, according to the test kit's instructions, on samples of the pool water at approximately the same times as the ORP sensor readings are taken. The frequency of the testing and length of time between tests may vary. At the time of each DPD test, the ORP sensor reading is noted. An unchanging DPD test value indicates that thorough dispersal of the DBDMH has provided homogeneous $Br_2$ concentration to the pool water. Once the DPH test value remains unchanged, the ORP sensor reading is typically stable at 700 mV±5 mV within a time in the range of about 1 to 10 hours.

In another illustrative embodiment of the invention, the method of the invention is carried out as previously described, except that (A) comprises preparing an aqueous mixture of water, sodium bromide and DMH. This aqueous mixture is then introduced into the pool water before adding the DBDMH in (B). Concentrations of sodium bromide and DMH are the same or similar to the ranges previously discussed, as is the DBDMH concentration.

In a comparative case, when a newly started up body of water, such as a swimming pool, is treated only with the biocide, N,N'-dihalo-5,5-dialkylhydantoin, in the manner described above, the ORP sensor reading drops continuously and must be repeatedly reset to the desired mV value for up to 3 weeks after the DPD test values are unchanged.

It will be apparent from the foregoing description that the present invention provides improved methods and systems for stabilizing the oxidation-reduction potential for halogen-based water treatment systems. These methods and systems are applicable to a wide range of halogenated water treatment systems, including recreational water such as swimming pools, whirlpool baths, hot tubs and spas.

The body of water being treated pursuant to this invention is either fresh water which has not been treated with an N,N'-dihalo-5,5-dialkylhydantoin biocidal agent, or is a body of water which does not contain dissolved residues resulting from prior addition to the water an N,N'-dihalo-5,5-dialkylhydantoin biocidal agent.

As used herein the term "water-soluble" and other terms of similar import designate that the compound has sufficient solubility in water to enable the results of this invention to be achieved. Such terms do not require that the compound be soluble in all proportions in water.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of enabling uniform control of bromine concentrations in a recreational body of water which has not been treated with an N,N'-dihalo-5,5-dialkylhydantoin biocidal agent or which does not contain residues resulting from prior addition thereto of an N,N'-dihalo-5,5-diallcylhydantoin biocidal agent, which method comprises conducting the following steps:

A) introducing into said body of water at least one water-soluble source of bromide ion and at least one dialkyihydantoin, in which the alkyl group each contain independently in the range of 1 to about 4 carbon atoms; and then B) introducing into said body of water at least one N,N'-dihalo-5,5-dialkylhydantoin in which one halogen atom is a bromine atom and the other halogen atom is either a bromine atom or a chlorine atom, and in which one alkyl group is a methyl group and the other alkyl group contains in the range of 1 to about 4 carbon atoms; and C) monitoring the oxidation-reduction potential (ORP) of said water, wherein said bromide ion and said dialkylhydantoin are introduced in step A) to stabilize the ORP of the water in an interval of time which is substantially shorter than the interval of time required to stabilize the ORP of the water without conducting step A)-has been inserted.

2. A method according to claim 1 wherein said body of water is a swimming pool.

3. A method according to claim 1 wherein said source of bromide ion is (i) at least one alkali metal bromide or (ii) at least one alkaline metal bromide, or (iii) both of (i) and (ii).

4. A method according to claim 1 wherein said source of bromide ion is sodium bromide.

5. A method according to claim 1 wherein step A) results in a bromide ion concentration in said body of water of about 5 ppmw to about 50 ppmw.

6. A method according to claim 1 wherein said dialkylhydantoin is dimethylhydantoin.

7. A method according to claim 1 wherein said at least one dialkyihydantoin is introduced into said body of water in an amount in the rang of about 15 ppmw to about 20 ppmw.

8. A method according to claim 1 wherein said at least one N,N'-dihalo-5,5-dialkyihydantoin is at least one 1,3-dibromo-5,5-dialkylhydantoin in which one alkyl group is a methyl group and the other alkyl group contains in the range of 1 to about 4 carbon atoms.

9. A method according to claim 1 wherein said at least one N,N'-dihalo-5,5-dialkyihydantoin is 1,3-dibromo-5,5-dimethylhydantoin.

10. A method according to claim 1 wherein said at least one N,N'-dihalo-5,5-dialkyihydantoin is (i) N,N'-bromochloro-5,5-dimethylhydantoin or (ii) a mixture of N,N'-bromochloro-5,5-dimethylhydantoin, 1,3-dichloro-5-ethyl-5-methylhydantoin, and 1,3-dichloro-5,5-dimethylhydantoin in which more than 50 wt % of said mixture is N,N'-bromochloro-5,5-dimethylhydantoin.

11. A method according to claim 1 wherein step B) results in an active bromine concentration in the range of about 1 ppmw to about 10 ppmw as active $Br_2$.

12. A method according to claim 1 wherein said body of water is a swimming pool equipped with an oxidation-reduction potential controller having an ORP sensor probe in contact with the water in the pool, wherein said source of bromide ion is sodium bromide, wherein said dialkylhydantoin is dimethylhydantoin, and wherein said at least one N,N'-dihalo-5,5-dialkyihydantoin is at least one 1,3-dibromo-5,5-dialkylhydantoin in which one alkyl group is a methyl group and the other alkyl group contains in the range of 1 to about 4 carbon atoms.

13. A method according to claim 12 wherein step A) results in a bromide ion concentration in said body of water of about 5 ppmw to about 50 ppmw, wherein said at least one dialkylhydantoin is introduced into said body of water in amount in the range of about 15 ppmw to about 20 ppmw, and wherein step B) results in an active bromine concentration in the range of about 1 ppmw to about 10 ppmw as active $Br_2$.

14. A method according to claim 13 wherein said at least one N,N'-dihalo-5,5-dialkylhydantoin is 1,3-dibromo-5,5-dimethylhydantoin.

15. A method according to claim 13 wherein said at least one N,N'-dihalo-5,5-dialkyihydantoin is (i) N,N'-bromochloro-5,5-dimethylhydantoin or (ii) a mixture of N,N'-bromochloro-5,5-dimethylhydantoin, 1,3-dichloro-5-ethyl-5-methylhydantoin, and 1,3-dichloro-5,5-dimethylhydantoin in which more than 50 wt % of said mixture is N,N'-bromochloro-5,5-dimethylhydantoin.

16. A method according to claim 1 wherein said body of water is equipped with an oxidation-reduction potential controller having oxidation-reduction potential sensor probe in contact with said body of water.

17. A method according to claim 16 wherein said body of water is a swimming pool.

18. A method of reducing the interval of time of stabilizing the oxidation-reduction potential of a recreational body of water which has not been treated with an N,N'-dibalo-5,5-dialkylhydantoin biocidal agent or which does not contain residues resulting from prior addition thereto of an N,N'-dihalo-5,5-dialkylhydantoin biocidal agent, which method comprises conducting the following steps:

A) introducing into said body of water at least one water-soluble source of bromide ion and at least one dialkylhydantoin, in which the alkyl group each contain independently in the range of 1 to about 4 carbon atoms; then B) introducing into said body of water at least one N,N'-dihalo-5,5-dialkylhydantoin in which one halogen atom is a bromine atom and the other halogen atom is either a bromine atom or a chlorine atom, and in which one alkyl group is a methyl group and the other alkyl group contains in the range of 1 to about 4 carbon atoms; and C) monitoring the oxidation-reduction potential (ORP) of said water, wherein said bromide ion and said dialkylhydantoin are introduced in step A) to stabilize the ORP of the water in an interval of time which is substantially shorter than the interval of time required to stabilize the ORP of the water without conducting step A).

19. A method according to claim 18 wherein said interval of time is in the range of about 1 to about 10 hours.

20. A method according to claim 18 wherein said interval of time is in the range of about 1 to about 6 hours.

21. A method according to claim 18 wherein said body of water is a swimming pool equipped with an oxidation-reduction potential controller having an ORP sensor probe in contact with the water in the pool, wherein said source of bromide ion is sodium bromide, wherein said dialkylhydantoin is dimethylhydantoin and wherein said at least one N,N'-dihalo-5,5-dialkylhydantoin is at least one 1,3-dibromo-5,5-dialkylhydantoin in which one alkyl group is a methyl group and the other alkyl group contains in the range of 1 to about 4 carbon atoms.

22. A method according to claim 21 wherein step A) results in a bromide ion concentration in said body of water of about 5 ppmw to about 50 ppmw, wherein said at least one dialkylhydantoin is introduced into said body of water in amount in the range of about 15 ppmw to about 20 ppmw, and wherein step B) results in an active bromine concentration in the range of about 1 ppmw to about 10 ppmw as active $Br_2$.

23. A method according to claim 22 wherein said at least one N,N'-dihalo-5,5-dialkylhydantoin is 1,3-dibromo-5,5-dimethylhydantoin.

24. A method according to claim 18 wherein said source of bromide ion is sodium bromide, wherein said dialkylhydantoin is dimethylhydantoin, wherein said at least one N,N'-dihalo-5,5-dialkylhydantoin is at least one 1,3-dibromo-5 5-dialkyihydantoin in which one alkyl group is a methyl group and the other alkyl group contains in the range of 1 to about 4 carbon atoms, and wherein said sodium bromide and said dimethylhydantoin are introduced into said body of water as a pre-mixed, pre-packaged composition containing in the range of about 2 to about 5 parts by weight of dimethylhydantoin per each by weight of sodium bromide.

25. A method according to claim 24 where said at least one 1,3-dibromo-5,5-dialkylhydantoin is 1,3-dibromo-5,5-dimethylhydantoin.

26. A method of enabling uniform control of bromine concentrations in a recreational body of water which experiences ORP bounce and contains an N,N'-dihalo-5,5-dialkylhydantoin biocidal agent, which method comprises conducting the following steps:

A) introducing into said body of water at least one water-soluble source of bromide ion and at least one dialkylhydantoin, in which the alkyl group each contain independently in the range of 1 to about 4 carbon atoms; and then B) introducing into said body of water at least one N,N'-dihalo-5,5-dialkylhydantoin in which one halogen atom is a bromine atom and the other halogen atom is either a bromine atom or a chlorine atom, and in which one alkyl group is a methyl group and the other alkyl group contains in the range of 1 to about 4 carbon atoms; and C) monitoring the oxidation-reduction potential (ORP) of said water, wherein said bromide ion and said dialkylhydantoin are introduced in step A) to stabilize the ORP of the water in an interval of time which is substantially shorter than the interval of time required to stabilize the ORP of the water without conducting step A).

27. A method according to claim 26 wherein step A) results in a bromide ion concentration in said body of water of about 5 ppmw to about 50 ppmw.

28. A method according to claim 26 wherein said at least one dialkylhydantoin is introduced into said body of water in an amount in the rang of about 15 ppmw to about 20 ppmw.

29. A method of shortening the period of time required for water treated with an N,N'-dihalo-5,5-dialkylhydantoin biocidal agent to reach the point at which the active bromine content of the treated water is at a suitable biocidal concentration as determined by means of an ORP controller equipped with an ORP sensor probe in contact with said water, said concentration verifiable as by a manual DPD test procedure, which method comprises introducing into said water at least one water-soluble source of bromide ion and at least one dialkyihydantoin in which the alkyl groups each contain independently in the range of 1 to about 4 carbon atoms; and then treating the water with N,N'-dihalo-5,5-dialkyihydantoin in which one halogen atom is a bromine atom and the other halogen atom is either a bromine atom or a chlorine atom, and in which one alkyl group is a methyl group and the other alkyl group contains in the range of 1 to about 4 carbon atoms; and monitoring the oxidation-reduction potential (ORP) of said water, wherein said bromide ion and said dialkylhydantoin are introduced into the water to stabilize the ORP of the water in a period of time which is substantially shorter than the period of time required to stabilize the ORP of the water without introducing said bromide ion and said dialkylhydantoin.

30. A method according to claim 29 wherein said water is water contained in a swimming pool, wherein said source of bromide ion is sodium bromide, and wherein introduction of said bromide ion results in a bromide ion concentration in said water of about 5 ppmw to about 50 ppmw.

31. A method according to claim 29 wherein said at least one dialkyihydantoin is dimethylhydantoin and wherein said at least one dialkyihydantoin is introduced into said water in an amount in the range of about 15 ppmw to about 20 ppmw.

32. A method according to claim 29 wherein said N,N'-dihalo-5,5-dialkyihydantoin is at least one 1,3-dibromo-5,5-dialkylhydantoin in which one alkyl group is a methyl group and the other alkyl group contains in the range of 1 to about 4 carbon atoms.

33. A method according to claim 29 wherein said N,N'-dihalo-5,5-dialkyihydantoin is 1,3-dibromo-5,5-dimethylhydantoin.

34. A method according to claim 29 wherein said period of time is in the range of about 1 to about 10 hours.

35. A method according to claim 29 wherein said period of time is in the range of about 1 to about 6 hours.

* * * * *